United States Patent [19]

King et al.

[11] Patent Number: 5,233,518

[45] Date of Patent: Aug. 3, 1993

[54] EXTRAPOLATIVE RECONSTRUCTION METHOD FOR HELICAL SCANNING

[75] Inventors: Kevin F. King, New Berlin; Carl R. Crawford, Milwaukee, both of Wis.

[73] Assignee: General Electric Company, Milwaukee, Wis.

[21] Appl. No.: 435,980

[22] Filed: Nov. 13, 1989

[51] Int. Cl.$^5$ ............................................. G06F 15/00
[52] U.S. Cl. .......................... 364/413.18; 364/413.17
[58] Field of Search ................... 364/413.18, 413.15, 364/413.16, 413.17, 413.19

[56] References Cited

U.S. PATENT DOCUMENTS

| | | | |
|---|---|---|---|
| 4,284,896 | 8/1981 | Stonestrom | 250/445 |
| 4,506,327 | 3/1985 | Tam | 364/413.19 |
| 4,630,202 | 12/1986 | Mori | 364/414 |
| 4,789,929 | 12/1988 | Nishimura et al. | 364/413.15 |
| 4,866,614 | 9/1989 | Tam | 364/413.25 |
| 4,888,693 | 12/1989 | Tam | 364/413.13 |
| 4,899,318 | 2/1990 | Schlumberger et al. | 364/413.25 |
| 4,922,421 | 5/1990 | Tam | 364/413.13 |
| 5,032,990 | 7/1991 | Eberhart et al. | 364/413.13 |
| 5,053,958 | 10/1991 | Tam | 364/413.13 |
| 5,073,911 | 12/1991 | Ozaki et al. | 364/413.15 |

Primary Examiner—Donald E. McElheny, Jr.
Assistant Examiner—Xuong Chung
Attorney, Agent, or Firm—Quarles & Brady

[57] ABSTRACT

A method of reducing image helical scanning; artifacts in computed tomography imaging systems divides 360° of projection data into two half scans. Separate weighting functions are applied to the two half scans and they are reconstructed to an image per conventional reconstruction methods. The weighting functions provide effective interpolation and extrapolation of the half scan data to a slice plane centered in the projection data. In one embodiment, the weighting functions are feathered with a cubic function to remove weighting induced image artifacts.

4 Claims, 5 Drawing Sheets

EXTRAPOLATIVE RECONSTRUCTION METHOD FOR HELICAL SCANNING

BACKGROUND OF THE INVENTION

This invention relates to computed tomography using helical scanning. More specifically, the invention relates to an image reconstruction method for reducing image artifacts that result from acquiring tomographic projection data in a helical scan.

As used herein, computed tomography shall refer to both tomography using "transmission imaging" that is, detecting radiation transmitted through the body being imaged, and "emission imaging", detecting radiation emitted from the body being imaged, e.g., such as that being emitted by radiopharmaceutical isotopes.

In a transmission imaging computed tomography system, an x-ray source is collimated to form a fan bean with a defined fan beam angle. The fan beam is orientated to lie within the x-y plane of a Cartesian coordinate system, termed the "imaging plane", and to be transmitted through an imaged object to an x-ray detector array orientated within the imaging plane. The detector array is comprised of detector elements which each measure the intensity of transmitted radiation along a ray projected from: the x-ray source to that particular detector element. The detector elements can be organized along an arc each to intercept x-rays from the x-ray source along a different ray of the fan beam. The intensity of the transmitted radiation is dependent on the attenuation of the x-ray beam along the ray by the imaged object.

The x-ray source and detector array may be rotated on a gantry within the imaging plane, around the imaged object, so that the fan beam intercepts the imaged object at different angles. At each angle, a projection is acquired comprised of the intensity signals front each of detector elements. The gantry is then rotated to a new angle and the process is repeated to collect a number of projections at different angles to form a tomographic projection set.

The acquired tomographic projection set is typically stored in numerical form for computer processing to "reconstruct" a slice image according reconstruction algorithms known in the art. The reconstructed slice images may be displayed on a conventional CRT tube or may be converted to a film record by means of a computer controlled camera.

In either emission or transmission computed tomography the detector array may be rectilinear rather than arcuate.

A typical computed tomographic study entails the imaging of a series of slices of an imaged object with the slices displaced incrementally along a z-axis perpendicular to the x and y axes, so as to provide a third spatial dimension of information. A radiologist may visualize this third dimension by viewing the slice images in order of position along the z-axis, or the numerical data comprising the set of reconstructed slices may be compiled by computer programs to produce shaded, perspective representations of the imaged object in three dimensions.

As the resolving power of computed tomography methods increases, additional slices are required in the z-dimension. The time and expense of a tomographic study increases with the number of slices required. Also, longer scan times increase the discomfort to the patient who must remain nearly motionless to preserve the fidelity of the tomographic reconstructions. Accordingly, there is considerable interest in reducing the time required to obtain a slice series.

The time required to collect the data for a series of slices depends in part on four components: a) the time required to accelerate the gantry to scanning speed, b) the time required to obtain a complete tomographic projection set, c) the time required to decelerate the gantry and d) the time required to reposition the patient in the z-axis for the next slice. Reducing the time required to obtain a full slice series may be accomplished by reducing the time required to complete any of these four steps.

The time required for acceleration and deceleration of the gantry may be avoided in tomographic systems that use slip rings rather than cables to communicate with the gantry. The slip rings permit continuous rotation of the discussed are equipped with slip rings or the equivalent to permit continuous rotation of over 360°.

The time required to acquire the tomographic data set is more difficult to reduce. Present CT scanners require on the order of one to two seconds to acquire the projection set for one slice. This scan time may be reduced by rotating the gantry at a faster speed. A higher gantry speed, in general, will reduce the signal-to-noise ratio of the acquired data by the square root of the factor of rotational rate increase. This may be overcome to some extent in transmission tomography devices by increasing the radiation output of the x-ray tube, but is subject to the power limits of such devices.

A reduction in patient repositioning time may be accomplished by translating the patient in the z-axis synchronously with the rotation of the gantry. The combination of constant patient translation along the z-axis during the rotation of the gantry and acquisition of projection data has been termed "helical scanning" and refers to the apparent path of a point on the gantry with respect to a reference point on the imaged body. As used herein, "helical scanning" shall refer generally to the use of continuous translation of the patient or imaged object during the acquisition of tomographic imaging data, and "constant z-axis scanning" shall refer to the acquisition of the tomographic data set without translation of the patient or imaged object during the acquisition period.

Continuous translation of the imaged object during scanning shortens the total scanning time required for the acquisition of a given number of slices by eliminating the length of time normally required for repositioning the patient between scans. However, helical scanning introduces certain errors with regard to the data in the acquired tomographic projection sets. The mathematics of tomographic reconstruction assumes that the tomographic projection set is acquired along a constant z-axis slice plane. The helical scan path clearly deviates from this condition and this deviation results in image artifacts in the reconstructed slice image if there is any significant change in the object in the z-axis. The severity of the image artifacts depends generally on the "helix offset" in the projection data, measured as the difference between the table locations of the scanned data and the z axis value of the desired slice plane. Errors resulting from helical scanning will be referred to collectively as "skew" errors.

Several methods have been used to reduce skew errors in helical scanning. A first approach disclosed in U.S. Pat. No. 4,630,202 issued Dec. 16, 1986, reduces the pitch of the helical scan and then averages the projection data of consecutive 360° tomographic projection sets. The effect is equivalent to using a detector array with a larger width along the z axis, which also moves less in the z direction during a rotation of the gantry, i.e. with a lesser scanning pitch. Skew errors are reduced using this method, but at the expense of additional scanning time necessitated by the lower scanning pitch. Thus, this method reduces, to some extent, the advantages to be gained by helical scanning.

Skew errors at the ends of the tomographic projection set may be reduced in conjunction with this approach by changing the weighting of the last and first projections of the consecutive 360° tomographic projection sets in the "averaging" process to give greater weight to the projection closest to the slice plane.

A second approach disclosed in U.S. Pat. No. 4,789,929 issued Dec. 6, 1988, also applies weighting to the projections of combined, consecutive 360° tomographic projection sets, but the weighting is a function of the helical offset of each projection at the given gantry angle. This approach of interpolating over 720° generally increases partial volume artifacts. Partial volume artifacts are image artifacts arising when certain volume elements of the imaged object contribute to only some of the projections of the projection set.

A third approach described in copending U.S. Pat. application Ser. No. 07/430,372, entitled: "Computerized Tomographic Image Reconstruction Method for Helical Scanning" and assigned to the same assignee as the present invention, uses a half-scanning technique to reduce the table motion during the acquisition of each slice. Projection data is acquired over 360° plus twice the fan beam angle of gantry rotation and interpolated to a slice plane. The reduced gantry motion corresponds to reduced table motion and hence certain helical scanning artifacts are reduced.

SUMMARY OF THE INVENTION

It is understood in the art, that a tomographic image may be prepared from projection data acquired over 180° plus the fan beam angle of gantry rotation. Generally, this result arises from the equivalence in attenuation of certain rays in projection acquired at gantry angles 180° apart. This method of reconstructing a tomographic image is termed "half scan" and ordinarily requires that the acquired data be weighted by a "half scan weighting function" prior to reconstruction of the image so as to deemphasize certain redundant data within each half scan.

The present invention reduces skew artifacts by reconstructing an image from the data of two half scans. However, by sharing the redundant data between the half scans, they may be acquired over only 360° of gantry rotation rather than 360° plus twice the fan beam angle of gantry rotation ordinarily required to collect two half scans. The sharing of redundant data that permits this compressed data acquisition, requires that the half scan data be extralpolated and interpolated to the slice plane.

In accordance with the invention, two partial projection sets of data acquired over 180° of gantry rotation are collected, one on each side of the slice plane. This data is divided into two half scan projection sets, each half scan being composed of data from both sides of the slice plane. The half scans are weighted to permit interpolation and extrapolation to the slice plane and the combined half scans are reconstructed to form an image.

It is one object of the invention to permit the acquisition of projection data for a single slice image over a shorter z-axis distance. For a given scan pitch, the use of half scans acquired in 360° rather than 360° plus twice the fan beam angle, requires less z-axis travel in a helical scan. This in turn concentrates the projections acquired at points closer to the slice plane and thus improves the accuracy of the interpolation and extrapolation and decreases partial volume artifacts.

It is another object of the invention to permit the acquisition of projection data for a single slice image over a shorter time period. Image artifacts may result from patient motion during the acquisition of the projection data of a tomographic projection set. For a given gantry speed, the use of half scans acquired in only 360° of gantry rotation permit the reconstruction of images that are less susceptible to motion artifacts.

It is another object of the invention to improve the efficiency of the half scanning process. By sharing redundant data between half scans, the total x-ray exposure to the patient may be reduced.

The foregoing and other objects and advantages of the invention will appear from the following description. In the description, reference is made to the accompanying drawings which form a part hereof and in which there is shown by way of illustration, a preferred embodiment of the invention. Such embodiment does not necessarily represent the full scope of the invention, however, and reference must be made therefore to the claims herein for interpreting the scope of the invention.

DETAILED DESCRIPTION OF THE PREFERRED EMBODIMENT

Figure 1:
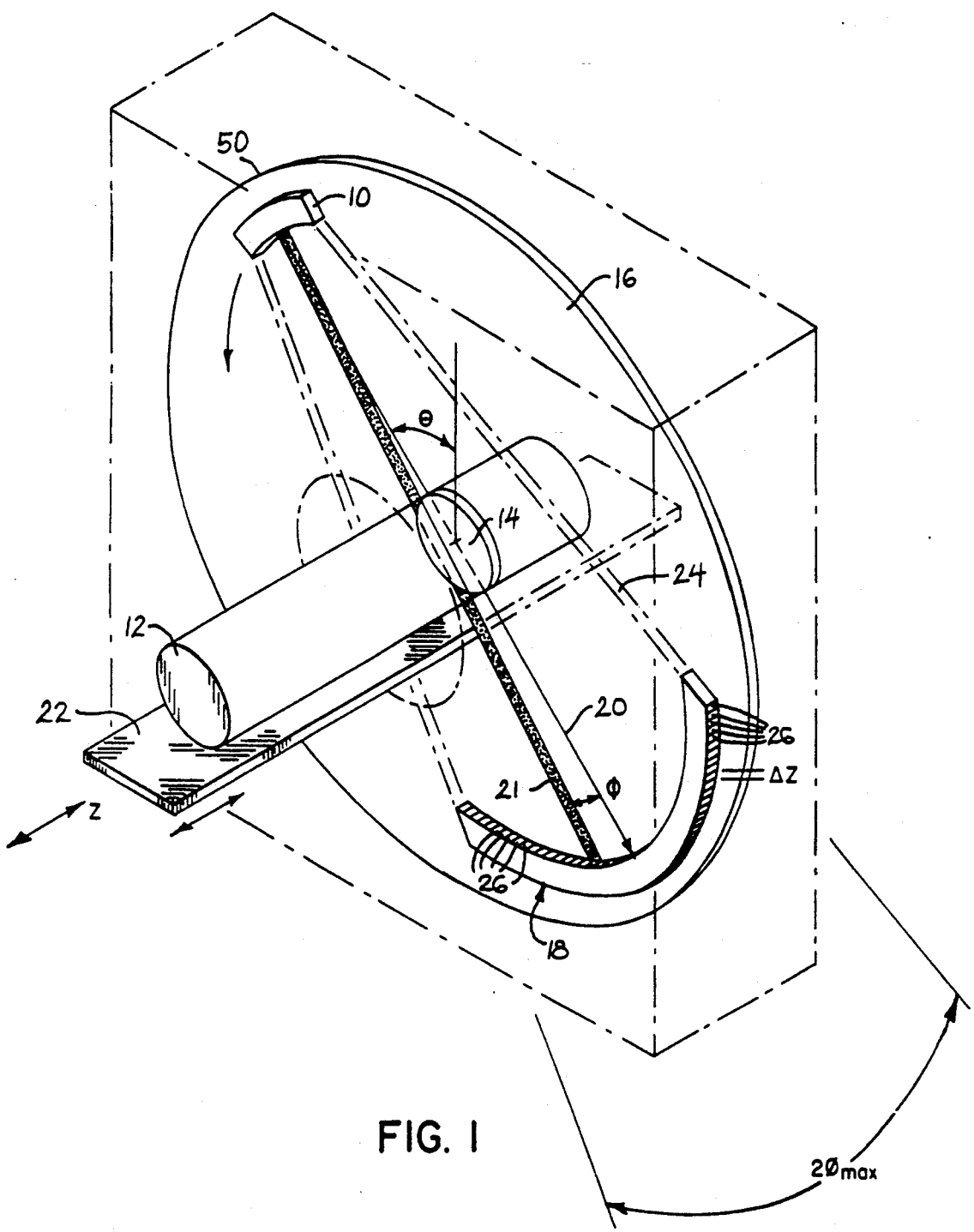
FIG. 1 is a pictorial representation of a CT apparatus including gantry, table and imaged object, and showing the relative angles and axes associated therewith.

Referring to FIG. 1, a CT gantry 16, representative of a "third generation" CT scanner includes an x-ray source 10 oriented to project a fan beam of x-rays 24 through imaged object 12 to detector array 18. The fan beam 24 is directed along an x-y plane of a Cartesian coordinate system, the "imaging plane", and subtends a "fan angle" of $2\phi_{max}$ as measured along the imaging plane. The detector array 18 is comprised of a number of detector elements 26 which together receive and detect a value proportional to the magnitude of a projected image resulting from the transmission of x-rays through the imaged object 12, or in the case of emission tomography, from the radiation emitted from the radiopharmaceutical isotopes within the imaged object 12. The angle $\phi$, measured from the centermost ray 20 of the fan beam 24, may identify each ray 21 of the fan beam 24 and its associated detector 26 and will be termed the fan beam angle.

The angular position $\theta$ of the gantry 16 with respect to the imaged object 12 is arbitrarily referenced to zero when the fan beam's center most ray 20 is vertical and directed downward. The gantry 16 is coupled to the gantry associated control modules 48 shown in FIG. 3 and to be described below, by means of slip rings 50 and is therefore free to rotate continuously through angles greater than 360° to acquire projection data.

The imaged object 12 rests on table 22 which is radiotranslucent so as to minimize interference with the imaging process. Table 22 may be controlled so that its upper surface translates along the z axis perpendicular to the x-y imaging plane, by moving the imaged object 12 across the imaging plane swept by the fan beam 24. For simplicity, it will be assumed henceforth that the table 22 moves at a constant velocity and therefore that the z axis position of the table 22 is proportional to the angular position $\theta$ of the gantry 16. Accordingly, the tomographic projections acquired may be defined either in terms of z or $\theta$.

Figure 2A:
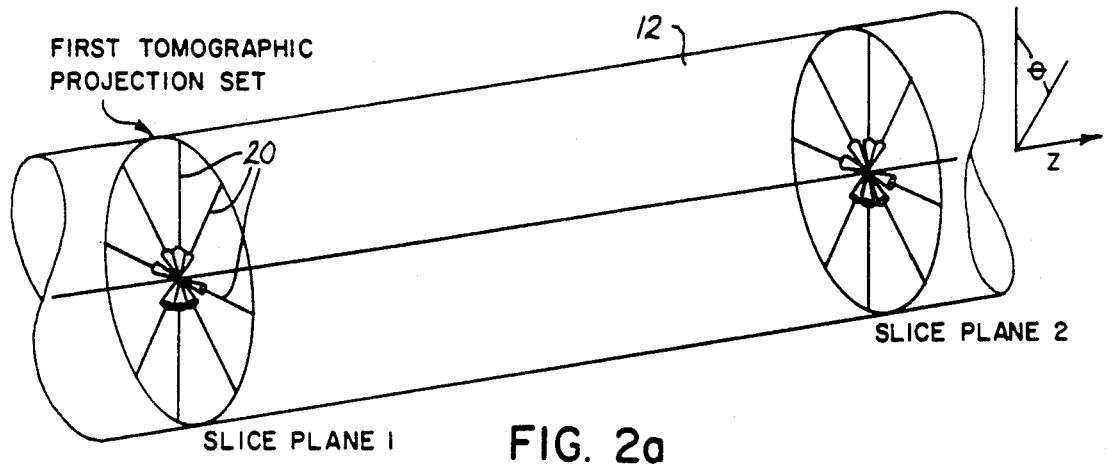
FIG. 2(a) and 2(b) are schematic illustrations of the imaged object of FIG. 1 showing the relative orientation gantry and imaging plane with respect to the imaged object for constant z axis scanning and helical scanning respectively. The pitch of the helical scanning is exaggerated for clarity.
Figure 2B:
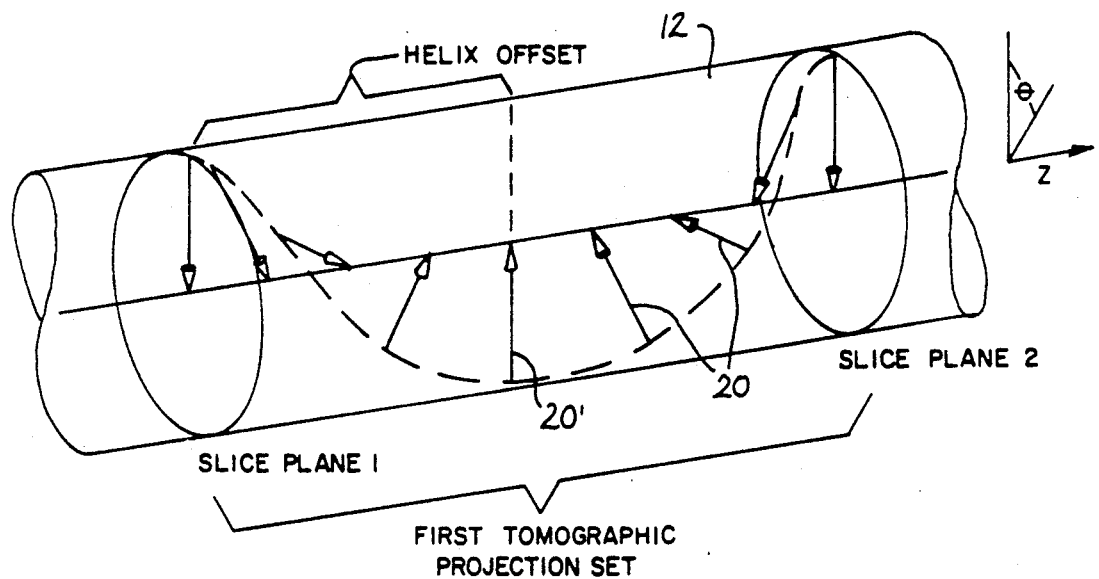

Referring to FIGS. 2(a) and 2(b), the angular position of the gantry and the z-axis position of the imaging plane with respect to the imaged object is shown by projection arrows 20 for a constant z-axis scan and a helical scan, respectively. In the constant z-axis scan, shown in FIG. 2(a) each tomographic projection set is acquired at a constant z-axis position and the imaged object is moved along the z-axis to the next slice plane between such acquisitions.

This differs from the helical scan in FIG. 2(b) where the z-axis position of the imaged object with respect to the imaging plane changes constantly during the acquisition of each tomographic projection set. Accordingly, arrows 20 trace a helix within the imaged object along the z-axis. The pitch of the helix will be referred to as the scanning pitch.

Figure 3:
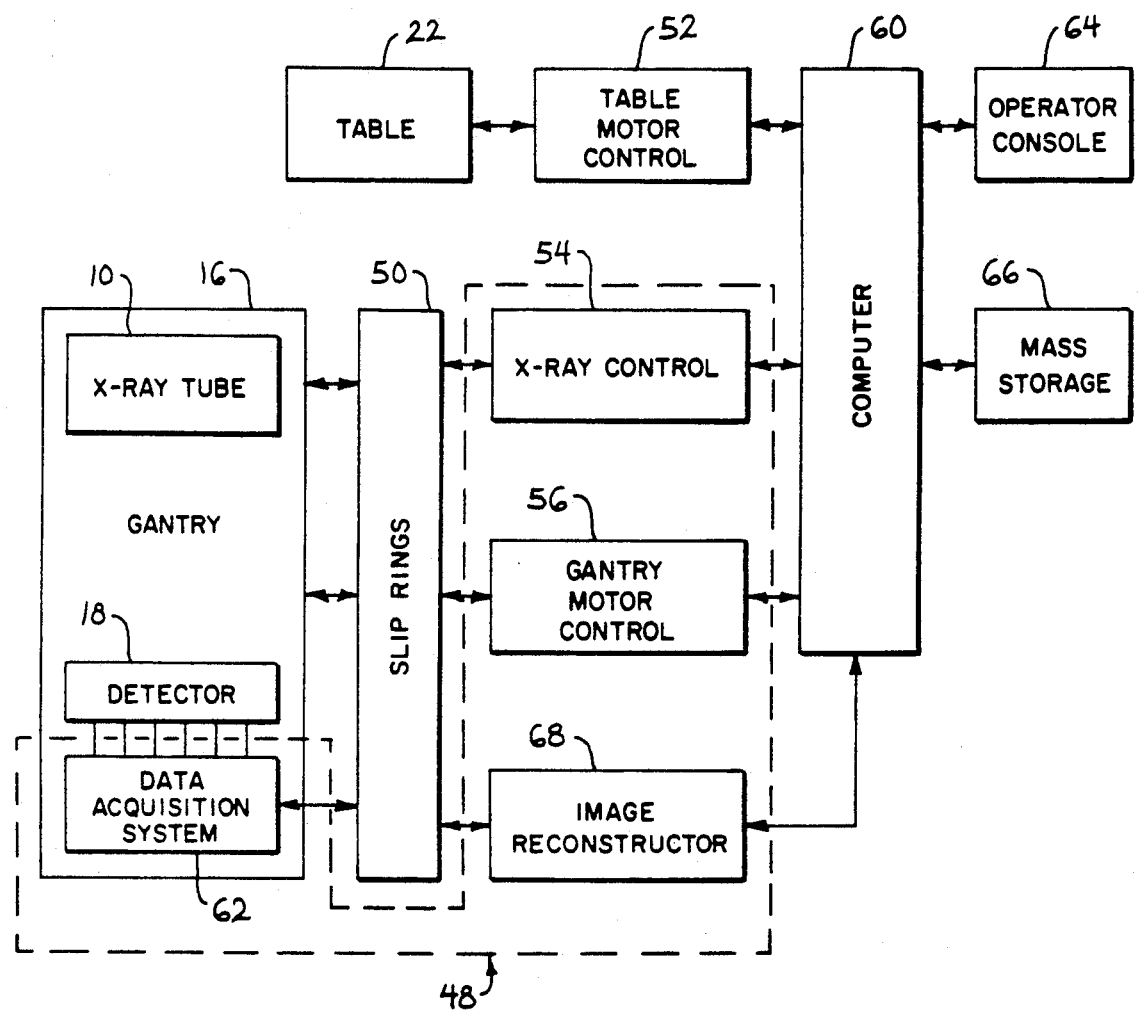
FIG. 3 is a block diagram of a CT control system that may be used with the CT apparatus of FIG. 1, and that is use for practicing the present invention.

Referring now to FIG. 3, the control system of a CT imaging system suitable for use with the present invention has gantry associated control modules 48 which include: x-ray control 54 which provides power and timing signals to the x-ray source 10, gantry motor controller 56 which controls the rotational speed and position of the gantry 16 and provides information to computer 60, and data acquisition system 62, regarding gantry position, and image reconstructor 68 which receives sample and digitized signals from the detector array 18 via the data acquisition system 62 to perform high speed image reconstruction according to methods known in the art. Each of the above can be connected to its associated elements on the gantry 16 via slip rings 50 and serves to interface computer 60 to various gantry functions.

The speed and position of table 22 along the z-axis, is communicated to and controlled by computer 60 by means of table motor controller 52. The computer 60 receives commands and scanning parameters via operator console 64 which is generally a CRT display and keyboard which allows the operator to enter parameters for the scan and to display the reconstructed image and other information from the computer 60. A mass storage device 66 provides a means for storing operating programs for the CT imaging system, as well as image data for future reference by the operator.

In conventional CT imaging, 360° of projection data, a full tomographic projection set, is acquired and reconstructed into a slice image. Alternatively, a tomographically reconstructed image may be derived from projection data acquired over less than 360° of gantry 16 rotation provided at least a minimum gantry rotation of 180° plus the fan beam angle is obtained. Image reconstruction using less than 360° of projection data will be termed "half scan" to distinguished it from "full scan" image reconstruction which requires 360° of projection data. The data used to reconstruct a half scan image will be termed a "half scan data set".

As a result of the fan beam geometry of the x-ray source 10 and the detector array 18, to be discussed further below, a half scan will contain certain duplicative data. This duplicative data ordinarily requires that the half scan data set be weighted with a "half scan weighting" function so that the duplicative data does not make a disproportionate contribution to the final image when incorporated with the non-redundant data. The weighting and reconstruction of images from a half scan data set are discussed in detail in "Optimal Short Scan Convolution Reconstruction for Fanbeam CT", Dennis L. Parker, Medical Physics 9(2) Mar./Apr. 1982.

Figure 4:
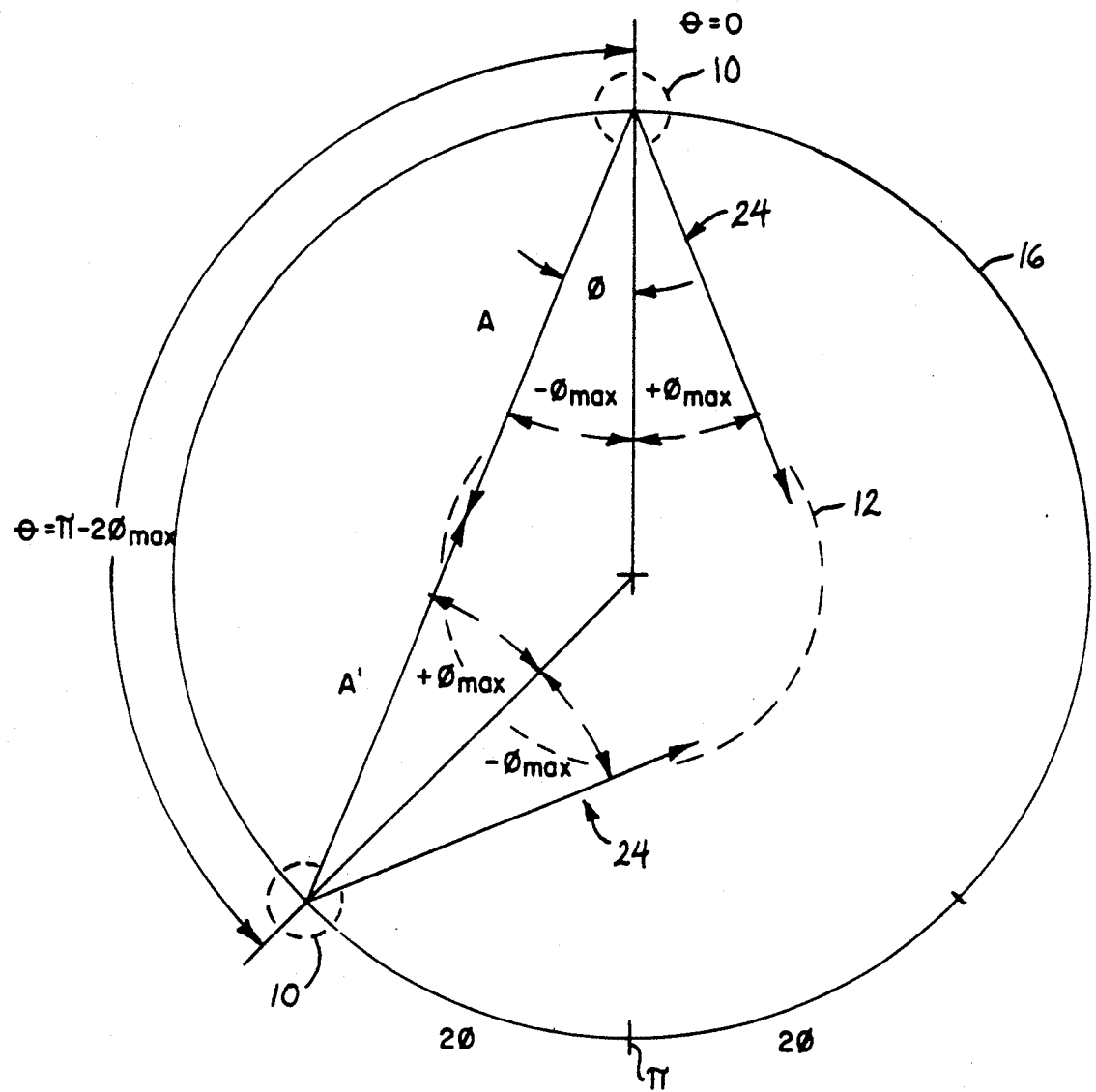
FIG. 4 is a diagram showing the geometry of an x-ray fan beam produced by the CT apparatus of FIG. 1 with the gantry shown positioned at two gantry angles $\theta$ as viewed along the z-axis.

The source of the duplicative data within a half scan acquired with a fan beam geometry may be demonstrated graphically. Referring to FIG. 4, a fan beam 24 at first gantry position $\theta=0$ includes ray A at angle $-\phi_{max}$ within the fan beam 24. The ray A is received by a detector element 26 (not shown) which produces a signal $P(\theta_1, -\phi_{max})$, where $\theta_1=0$, proportional to the line integral of the absorption of the x-ray radiation along ray A by imaged object 12. At a second fan beam 24 at second gantry position $\theta_2=\pi-2\phi_{max}$, it will be appreciated that the same line integral absorption measured along ray A in the first gantry position, is also measured along ray A' in the angle second gantry position, where ray A' is at angle $+\phi_{max}$ within the fan beam 24. The x-ray along ray A' is received by a detector element 26 (not shown) which produces a signal $P(\theta_2, \phi_{max})$. The identity of the measurements along ray A and A' may be generalized by the following relationship:

$$P(\theta, \phi) = P(\theta + \pi + 2\phi, -\phi) \tag{1}$$

where $\theta$ and $\phi$ are any gantry angle and any fan beam angle respectively. In helical scanning, data whose rays are equivalent by equation one, may nevertheless have different values as a result of the motion of the table during the gantry rotation. The term "redundant data" will be used to refer to this data within each half scan whose rays are related by equation 1 even though the values of the data may differ as a result of the helical scanning.

Figure 5A:
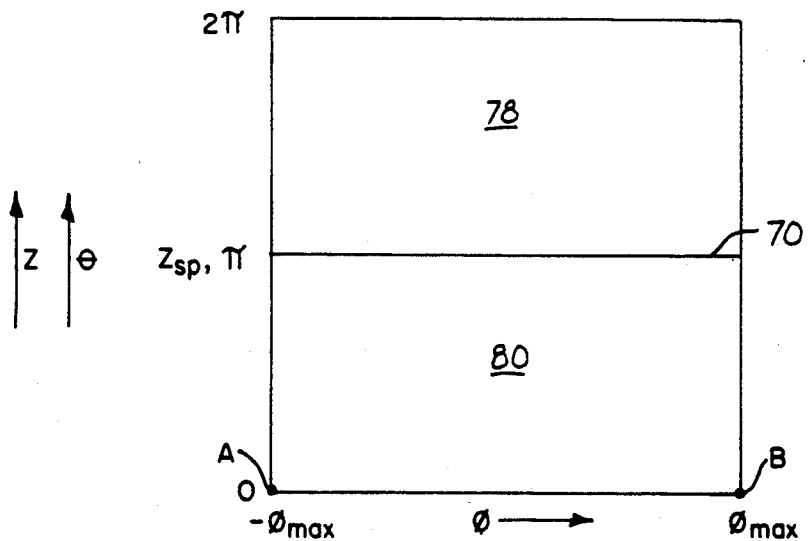
FIG. 5(a) is a graphical representation of the arguments $\theta$ and $\phi$ associated with the projection data of two partial projection sets acquired in a helical scan with the CT apparatus of FIG. 1.

In the present invention, two consecutive partial projection sets of tomographic data are acquired over a gantry 16 rotation of $2\pi$ radians (360°). During the acquisition of these projection sets, the table 22 and hence the imaged object 12 are advanced along the z-axis. Referring to FIG. 5(a), the arguments $\theta$ and $\phi$ for data for this first and second partial projection sets are shown schematically. Lines parallel to AB represent projections taken at gantry position $\theta$ and includes detector signals from angles $\phi$: $-\phi_{max} < \phi < +\phi_{max}$. The gantry angle $\theta$ of the projection along line AB is arbitrarily assigned to 0 and is the first projection of the first partial projection set. Successive projections are acquired at increasing gantry angles $\theta$ up to $\phi = \pi$ radians while the table 22 is advanced along the z-axis, per helical scanning techniques discussed above.

When the gantry angle reaches $\phi = \pi$ radians, shown by line 70 on FIG. 5(a), the first partial projection set 80 is complete and the slice plane $z_{sp}$ of the imaged object 12 has been aligned with the imaging plane. A second partial projection set 78 is then initiated starting at gantry angle $\phi = \pi$ and continuing to gantry angle $\phi = 2\pi$.

Figure 5B:
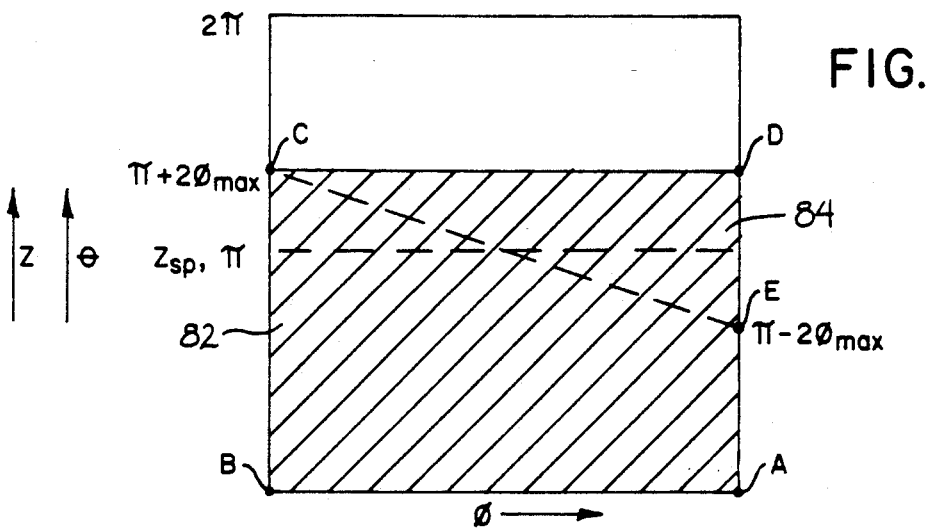
FIG. 5(b) is a graphical representation of a first half scan formed from the partial projection sets of FIG. 5(a)

Referring to FIG. 5(b), a first half scan 82 may be formed from this first and second partial projection sets 80 and 78. A half scan must contain at least $\pi + 2\phi_{max}$ radians of projections in order to reconstruct a image, and therefore, the half scan 82 includes data from $\theta = 0$ to $\theta = \pi + 2\phi_{max}$ and is shown by the shaded area in FIG. 5(b) between lines AB and CD, where CD is defined as $\theta = \pi + 2\phi_{max}$.

The first half scan 82 contains redundant data per equation (1) above, indicated by the triangular area 84, and including data between the line CD and line CE where CE is defined as $\theta = \pi - 2\phi$.

Ordinarily, the redundant data in the half scan is combined with the other data of the half scan by means of a half scan weighting function. In the present invention, however, a half scan 82', is formed without redundant data from the area ABCE. Specifically, the redundant data of triangular area 84 is not included within the first half scan 82'. A second half scan 86, also without redundant data, is formed of area ECGF where line GF is defined as $\theta = 2\pi$, and shown as the shaded region in FIG. 5(c). It summary, two half scan projection sets 82' and 86 may be formed from a total of $2\pi$ of projection data such that neither half scan contains redundant data. It should be noted however that each half scan embraces data from both sides of the slice plane indicated by line 70 at $\theta = \pi$.

Per equation (1), the data in the first half scan 82' may be matched to complementary data in the second half scan 86. Complimentary data is projection data in different half scans that would measure the same ray though the imaged object if the imaged object did not translate along the z axis. The complementary data of the two half scans 82' and 86 may be combined mathematically to estimate the values of an effective third half scan projection set (not shown) taken at the slice plane 70. As a result of the division of the partial projection sets 78 and 80 into half scans 82' and 86, however, the complementary data of half scans 82' and 86 is not necessarily on opposite sides of the slice plane 70 and hence extrapolation as well as interpolation must be used to derive the data for the slice plane 70.

Figure 5C:
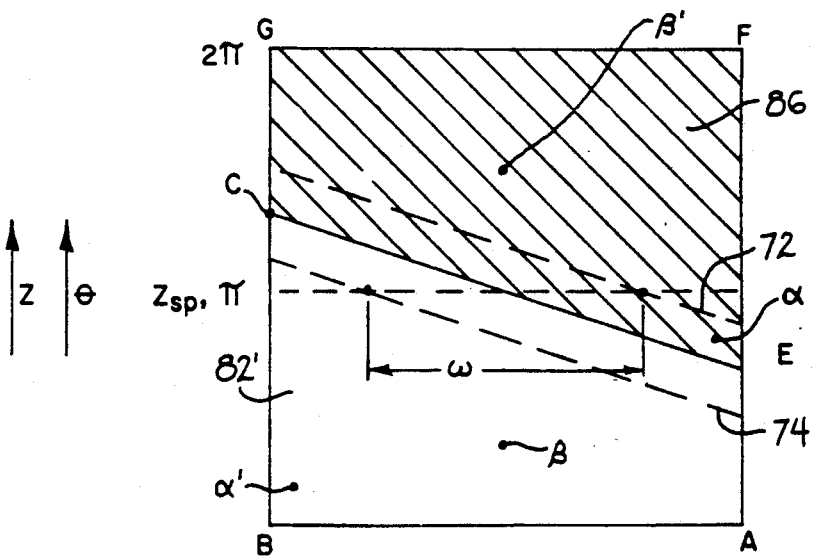
FIG. 5(c) is a graphical representation of a first and second half scan formed from the partial projection sets of FIG. 5(a).

For example, referring to FIG. 5(c), point $\alpha$ within the first partial projection set 80 and the second half scan 86 is complementary to $\alpha'$ which is on the same side of the slice plane 70 as is $\alpha$. Conversely, point $\beta$ positioned along line $\phi = 0$ is complementary to $\beta'$ on the opposite side of the slice plane 70. Therefore in the former case, the slice plane data must be extrapolated from the complementary points $\alpha$ and $\alpha'$ whereas in the latter case, the slice plate value may be interpolated from the complementary points $\beta$ and $\beta'$.

The extropolation process produces values that are outside of these of the data elements forming the basis for the extrapolation, and is therefore is less predictable than the interpolation process. For this reason, it was expected that the extrapolation would introduce its own artifacts. However, no adverse effects of the extrapolation have been detected.

For reasons of computation efficiency, a slice plane half scan is not first derived from the first and second half scans 82' and 86 but rather a weighting function is applied to the first and second half scans 82' and 86 and the combined first and second half scans 82' and 86 are reconstructed as a full scan, the extrapolation and interpolation being implicit in the reconstruction process.

For two complementary data elements $P(\theta_1, \phi_1)$ acquired at $Z_1$, and $P(\theta_2, \phi_2)$ acquired at $z_2$, linear interpolation or extrapolation to a slice plane data element $P(\phi_3, \phi_3)$ acquired at $z_{sp}$, may be performed by weighting the complementary points with weighting functions $w_1$, $w_2$ such that:

$$w_1 = \frac{z_2 - z_{sp}}{z_2 - z_1} \quad (2)$$

$$w_2 = \frac{z_{sp} - z_1}{z_2 - z_1} \quad (3)$$

where $$P(\phi_3, \phi_3) = w_1 P(\phi_1, \phi_1) + w_3 P(\phi_2, \phi_2)$$

In a helical scan with constant table and gantry speed, the table position z is proportional to gantry angle $\theta$ and hence the weighting functions may be rewritten as:

$$w_1 = \frac{\theta_2 - \theta_{sp}}{\theta_2 - \theta_1} \quad (4)$$

$$w_2 = \frac{\theta_{sp} - \theta_1}{\theta_2 - \theta_1} \quad (5)$$

By arbitrarily defining the gantry angle at the slice plane as $\pi$, and referring to the equivalence of equation (1) above for complementary data points, i.e., $\theta_2 = \theta_1 + \pi + 2\phi_1$, the following simplification may be made:

$$w_1 = 1 + \frac{\theta_1 - \pi}{\pi + 2\phi_1} \quad (6)$$

$$w_2 = 1 + \frac{\pi - \theta_2}{\pi - 2\phi_2} \quad (7)$$

Therefore, the data in the first half scan projection set 82' is multiplied by the weight $$w_1(\theta, \phi) = 1 + \frac{\theta - \pi}{\pi + 2\phi} \quad (8)$$

while the data in the second half scan projection set is multiplied by the weight $$w_2(\theta, \phi) = 1 + \frac{\pi - \theta}{\pi - 2\phi} \quad (9)$$

The entire projection set is then reconstructed according to conventional full scan reconstruction techniques known to those of ordinary skill in the art.

Referring still to FIG. 5(c), the above weights have different values at the line CE separating the half scan projection sets. This creates a discontinuity between consecutively acquired projection data which produces streak artifacts in the final image. The discontinuity may be eliminated by feathering $w_1$ and $w_2$ near the interface of the two half scans on either side of line CE within lines 72 and 74 parallel to line CE.

Specifically, $w_2$ is multiplied by $f(\phi)$ and the product applied to the data of both half scans 82′ and 86 and $w_1$ is multiplied by $1-f(\phi)$ and the product applied to the data of both half scans 82′ and 86 where:

$$f(\phi) = \begin{cases} 0 & \text{for } \phi < \phi_c - \omega/2 \\ 3x^2(\phi) - 2x^3(\phi) & \text{for } \phi_c - \omega/2 \leq \phi \leq \phi_c + \omega/2\phi \\ 1 & \text{for } \phi > \phi_c + \omega/2 \end{cases} \quad (10)$$

and where $$x(\phi) = \frac{\phi - \phi_c}{\omega} + .5 \quad (11)$$

and $$\phi_c = \frac{\pi - \theta}{2} \quad (12)$$

$\omega$ is feathering width over which the two weighting functions are combined and is the horizontal separation of lines 72 and 74. A value of $\omega$ equivalent angle subtended by ten detector elements 26 is found sufficient. The function $3 \times 2(\phi) - 2 \times 3(\phi)$ controls of feathering and is chosen because it varies between zero and one.

Many modifications and variations of the preferred embodiment will still be within the spirit and scope of the will be apparent to those with ordinary skill in the art. For example, other interpolation or extrapolat methods may be used including those using data from a half scans before and after the first and second scans and using higher order interpolation methods. It should also be noted that the order of the weighting reconstruction is not critical and that alternatively, images may be reconstructed from the half scans and the resulting images weighted and combined after the reconstruction. Further this method may be utilized in situations where the gantry does not move at a constant speed with respect to the table, provided the z-axis position associated with each data element may be determined. Finally, for the purposes of simplifying the discussion, it has been assumed that the gantry is positioned at $\pi$ radians when the slice plane is crossed. Clearly, any starting gantry angle is acceptable, provided the partial projection sets are properly referenced from the gantry position at the slice plane.

We claim:

1. A method of producing a tomographic image of an image object from data acquired in a helical scan, the data collected in a series of fan beam projections at a plurality of gantry angles $\theta$ about a z axis and within an image plane, the fan beam projections including a plurality of data at fan beam angles $\phi$, comprising the steps of:
    a) identifying a slice plane $z_{sp}$ relative to the imaged object and parallel to he image plane;
    b) moving the imaged object along the z-axis and rotating the gantry so that the imaging plane crosses the slice plane at a gantry angle of $\pi$;
    c) acquiring a first partial projection set of data for $\pi$ radians of gantry rotation prior to the imaging plane crossing the slice plane;
    d) acquiring a second partial projection set of data for $\pi$ radians of gantry rotation subsequent to the imaging plane crossing the slice plane;
    e) dividing the data of the first and second partial projection sets into a first and second half scan projection set each half scan projection set including projection data on both sides of the imaging plane;
    f) extrapolating and interpolating the data of the first and second half scan data to data at the slice plane; and
    g) reconstructing a tomographic image from the slice plane data.

2. The method of claim 1 where the first and second data sets are extrapolated and interpolated by applying a first weighting function to the data of the first half scan and applying a second weighting function to the data of the second half scan and reconstructing the combined first and second half scan as a full scan.

3. The method of claim 2 wherein the half scan data is associated with a corresponding gantry angle $\theta$ and fan beam angle $\phi$ and first weighting function is $w_1$ and the second weighing function is $w_2$ such that:

$$w_1(\theta,\phi) = 1 + \frac{\theta - \pi}{\pi + 2\phi}$$

$$w_2(\theta,\phi) = 1 + \frac{\pi - \theta}{\pi - 2\phi}$$

4. The method of claim 1 where the first and second data sets are extrapolated and interpolated by applying the product of a first weighting function and a first feathering function to the data of the first and second half scan and applying the product of a second weighting function and a second feathering function to the data of the first and second half scan and reconstructing the combined first and second half scan as a full scan.

* * * * *

UNITED STATES PATENT AND TRADEMARK OFFICE
CERTIFICATE OF CORRECTION

PATENT NO. : 5,233,518
DATED : August 3, 1993
INVENTOR(S) : Kevin F. King et al.

It is certified that error appears in the above-identified patent and that said Letters Patent is hereby corrected as shown below:

| | |
|---|---|
| Col. 2, line 18 | "of the discussed" should be -- of the gantry. Hereafter, it will be assumed that the CT systems discussed --. |
| Col. 4, lines 5 & 6 | "the use of half scans" should be -- the use of two half scans --. |
| Col. 4, lines 39 & 40 | "orientation gantry" should be -- orientation of the gantry --. |
| Col. 8, line 17 | "$P(\theta_1,\phi_1))$" should be -- $P(\theta_1,\phi_1)$ --. |
| Col. 8, line 18 | "$z_1$, and" should be -- $z_1$, and --. |
| Col. 8, line 33 | "$P(\phi_3,\phi_3) = w_1 P(\phi_1,\phi_1) + w_3 P(\phi_2,\phi_2)$" should be -- $P(\theta_3,\phi_3) = w_1 P(\theta_1,\phi_1) + w_2 P(\theta_2,\phi_2)$. |
| Col. 9, line 37 | "controls of feathering" should be -- controls the rate of feathering --. |
| Col. 9, line 38 | "varies between" should be -- varies smoothly between --. |
| Col. 9, line 40 | "embodiment will" should be -- embodiment which will --. |

UNITED STATES PATENT AND TRADEMARK OFFICE
CERTIFICATE OF CORRECTION

PATENT NO. : 5,233,518
DATED : August 3, 1993
INVENTOR(S) : Kevin F. King et al.

It is certified that error appears in the above-identified patent and that said Letters Patent is hereby corrected as shown below:

| | |
|---|---|
| Col. 9, line 41 | "the will be" should be -- the invention will be --. |
| Col. 9, line 42 | "extrapolat methods" should be -- extrapolation methods --. |
| Col. 9, line 43 | "from a" should be -- from additional --. |
| Col. 9, line 44 | "second scans" should be -- second half scans --. |
| Col. 10, line 12 (Claim 1) | "to he image" should be -- to the image --. |

Signed and Sealed this

Twenty-ninth Day of March, 1994

*Attest:*

BRUCE LEHMAN

*Attesting Officer*   *Commissioner of Patents and Trademarks*